United States Patent [19]

Stein et al.

[11] 4,373,812
[45] Feb. 15, 1983

[54] CUVETTE ASSEMBLY

[75] Inventors: Bernard Stein, Andover; Hamid Keramaty, Lexington; Romas A. Brickus, Dorchester, all of Mass.

[73] Assignee: Instrumentation Laboratory Inc., Lexington, Mass.

[21] Appl. No.: 247,351

[22] Filed: Mar. 25, 1981

[51] Int. Cl.³ .......................................... G01N 21/07
[52] U.S. Cl. ........................... 356/246; 356/427; 422/72
[58] Field of Search .............. 356/246, 427, 440; 422/72

[56] References Cited

U.S. PATENT DOCUMENTS

| | | | |
|---|---|---|---|
| 3,586,484 | 6/1971 | Anderson | 23/230 |
| 3,759,666 | 9/1973 | Hill | 23/230 B |
| 3,798,459 | 3/1974 | Anderson | 250/218 |
| 3,813,031 | 5/1974 | Anderson | 233/26 |
| 3,829,223 | 8/1974 | Hamel | 356/246 |
| 3,873,217 | 3/1975 | Anderson | 356/246 |
| 3,899,296 | 8/1975 | Mailen | 23/259 |
| 4,123,173 | 10/1978 | Bullock | 356/246 |
| 4,226,531 | 10/1980 | Tiffany | 356/246 |

Primary Examiner—Vincent P. McGraw

[57] ABSTRACT

An improved analytical cuvette assembly includes structure defining a first chamber region that has a loading port through which a first reaction component is introduced for storage, structure defining a second chamber region having a loading port through which a second reaction component is introduced for storage, and barrier structure between the first and second chamber regions that has a crest portion that defines the lower edge of a transfer passage between the two chamber regions. The second chamber region includes an analysis region where the reaction product resulting from mixture of the two reaction components is subjected to analysis. Each chamber region is defined by opposed planar side wall surfaces and a planar base wall surface, and capillary flow inhibiting structure extends from the crest of the barrier structure along the intersection between a planar surface portion of the barrier structure and the side wall surface and along at least a portion of the intersection of the side wall surfaces and the base surface.

9 Claims, 7 Drawing Figures

U.S. Patent      Feb. 15, 1983      4,373,812
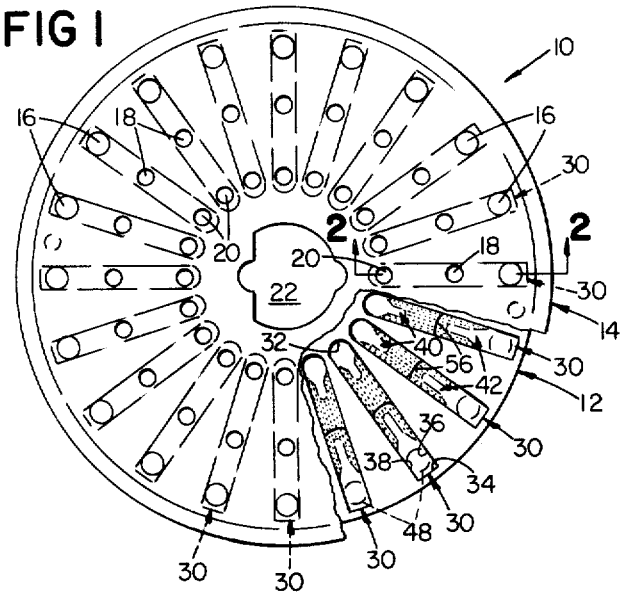
FIG 1
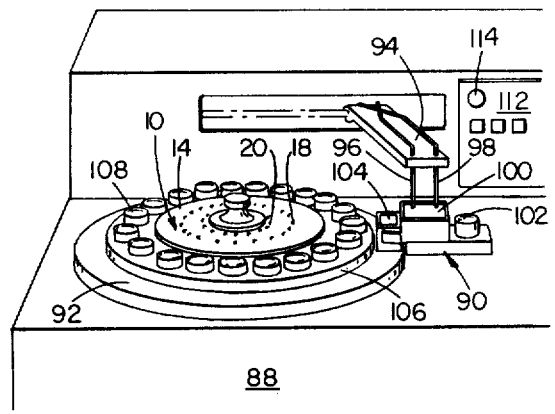
FIG 7
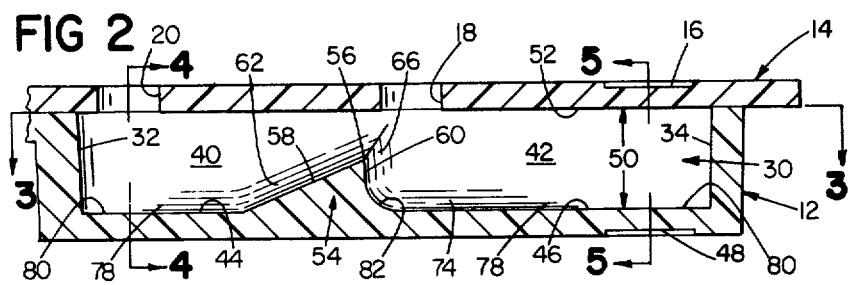
FIG 2
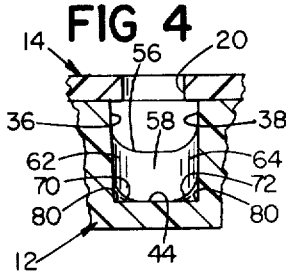
FIG 4
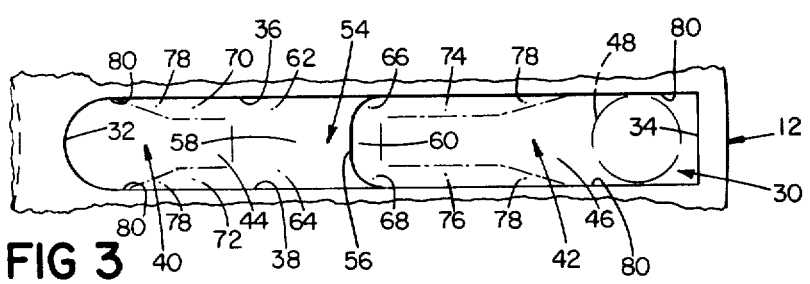
FIG 3
FIG 5
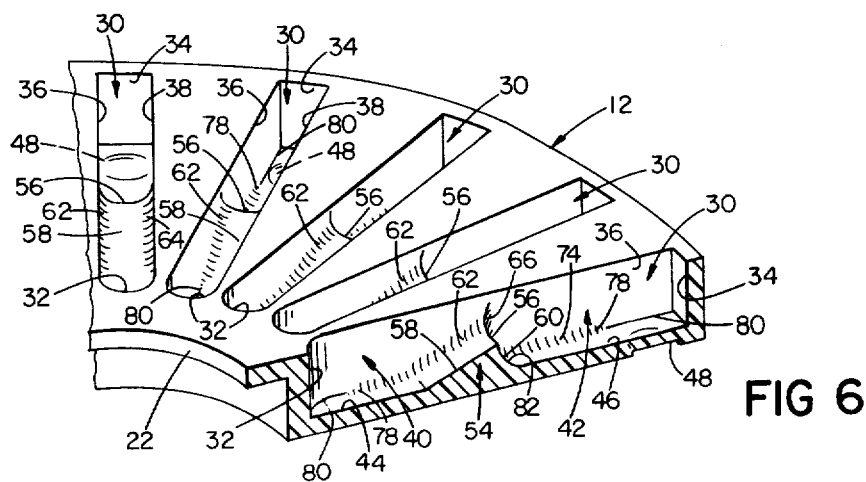
FIG 6

CUVETTE ASSEMBLY

This invention relates to analytical systems, and more particularly to cuvette assemblies of the plural compartment type for use in analytical systems.

A number of chemical analysis systems employ a plural compartment type of cuvette assembly which includes separate chamber portions for initially storing reagent materials separately and then transferring reagent material from one compartment to another for mixing and reaction, and subsequent analysis by the cooperating instrument of the reaction in the analysis region. A cuvette assembly of this type as disclosed in Tiffany et al. U.S. Pat. No. 4,226,531 is a rotor that has a circumferential array of spaced elongated radially extending cuvettes, each of which has two chambers each with an associated loading port. In use, sample to be analyzed (frequently with supplemental reagent material) is introduced into one chamber and a second reagent material is introduced into the second chamber. The rotor disclosed in the above patent has twenty cuvettes that are loaded successively with automated loading equipment, small quantities of sample (2-20 microliters) being loaded into first chambers, and reagents in quantities up to 200 microliters being loaded into second chambers. The loaded cuvette rotor is then transferred to an analyzer for photometric and/or fluorescence analysis. At the start of analysis, the rotor assembly is first spun at 100 rpm, then accelerated to 4000 rpm in about one second, then braked to a full stop, and then brought to 1000 rpm for analysis.

Numerous analytical tests are performed with this analyzer including, for example, glucose, creatinine, CPK, SGOT, and enzyme immuno assays. It has been found that in a number of the tests, including the enzyme immuno assays and to a lesser extent the triglyceride, glucose, creatinine and cholesterol tests, there is an unacceptable tendency of spontaneous mixing of reagents between the two chamber compartments, this mixing occuring in the case of some tests in less than four minutes after loading, while the loading and incubation sequence may take fifteen minutes or more.

In accordance with the invention there is provided an improved analytical cuvette assembly for receiving and separately storing two reaction components, and in a second condition mixing the two reaction components together to form a reaction product for analysis. The cuvette assembly includes structure defining a first chamber region that has a loading port through which a first reaction component is introduced for storage, structure defining a second chamber region having a loading port through which a second reaction component is introduced for storage, and barrier structure between the first and second chamber regions that has a crest portion that defines the lower edge of a transfer passage between the two chamber regions. The second chamber region includes an analysis region where the reaction product resulting from mixture of the two reaction components is subjected to analysis. Each chamber region is defined by opposed planar side wall surfaces and a planar base wall surface, and capillary flow inhibiting structure extends from the crest of the barrier structure along the intersection between a planar surface portion of the barrier structure and the side wall surface and along at least a portion of the intersection of the side wall surfaces and the base surface.

Preferably, the capillary flow inhibiting structure is a smoothly curved surface portion of radius greater than 0.75 millimeter that extends along the intersection between planar surfaces of the side walls, the barrier structure and the base wall structure and in a particular embodiment the smoothly curved surface portion has a radius of about 1.5 millimeter. Preferably each chamber region also includes capillary flow facilitating structure extending along each intersection between a chamber side wall surface and a chamber base wall surface at a location more remote from the barrier structure than the capillary flow inhibiting structure which tends to draw reagent material away from the barrier during the loading operation thereby reducing the "head" pressure; and in particular embodiments this capillary flow facilitating structure is a wall intersection less than 0.75 millimeter in radius.

In a particular embodiment, the cuvette assembly is a multicuvette rotor disc that has a circumferential array of elongated radially extending cuvettes, each of which has two radially spaced chamber regions with a barrier structure between the two regions and capillary flow inhibiting structure in each chamber region. Each cuvette has a width of about ½ centimeter, and a length of about four centimeters, and has an analytical region defined by a pair of opposed optical windows adjacent the outer periphery of the rotor disc, and the rotor disc comprises a one-piece body member of molded transparent material in which the barrier structure and capillary flow inhibiting structure of each cuvette is formed and a one-piece cover member of molded transparent material in which loading ports are formed and which is secured to the body member with continuous seals extending around each cuvette. The barrier structure in each cuvette includes a ramp surface inclined at less than 30° that forms an outer wall of the first chamber region and a vertical surface that forms an inner wall of the second chamber region with the loading port of each cuvette located adjacent the inner portion of the chamber region and the crest of the barrier about ¼ centimeter above the chamber base surfaces.

In cuvettes in accordance with the invention, spontaneous mixing of sample and reagent is delayed significantly (in preferred embodiments, the delay in spontaneous mixing being over eight times as long as the interval before premixing in prior art cuvette assemblies of the type disclosed in the above-mentioned Tiffany et al. patent) without increase in the size of the rotor or decrease in the number or size of the cuvettes.

Other features and advantages of the invention will be seen as the following description of a particular embodiment progresses, in conjunction with the drawings, in which:

FIG. 1 is a top plan view (with portions broken away) of a multi-cuvette rotor assembly in accordance with the invention;

FIG. 2 is a sectional view taken along the line 2—2 of FIG. 1;

FIG. 3 is a top plan view taken along the line 3—3 of FIG. 2 showing a top plan view of a cuvette;

FIGS. 4 and 5 are sectional views taken along the lines 4—4 and 5—5 respectively of the cuvette shown in FIG. 2;

FIG. 6 is a perspective view of a portion of the base of the rotor shown in FIG. 1; and FIG. 7 is a view of the loader mechanism used with the rotor of FIG. 1.

DESCRIPTION OF PARTICULAR EMBODIMENT

The rotor assembly 10 shown in FIG. 1 has a diameter of about ten centimeters and an overall height of about three-quarter centimeter and is formed of an injection molded acrylic body member 12 and an injection molded acrylic cover member 14 that has the desired transparency, chemical resistance, and optical characteristics for photometric analysis. The cover member 14 is a flat circular disc that has a circumferential array of recessed optical windows 16, an outer circumferential array of loading ports 18, an inner circumferential array of loading ports 20, and a substantially "D" shaped central opening 22. Body member 12 has a circumferential array of twenty individual cuvettes 30, each of which has a length of about four centimeters between a cylindrical inner wall 32 and a planar outer wall 34; and a width of about 0.45 centimeter between parallel planar side walls 36, 38. Each cuvette has an inner chamber 40 which is loaded through port 20 and an outer chamber 42 which is loaded through port 18. Each chamber has a planar base wall surface 44, 46 respectively and formed in the base of chamber 42 is a recessed optical window 48 aligned with an optical window 16 to provide an analysis region 50 that has an optical path length of one-half centimeter between cuvette base surface 46 and the parallel inner surface 52 of cover 14. In each cuvette 30 is barrier structure 54 that has a radial length of about six millimeters, a crest 56 that has a height of about ¼ centimeter, a planar ramp surface 58 inclined at about 22° that forms the rear wall of cuvette chamber 40 and a planar vertical surface 60 that forms the inner wall of cuvette chamber 42, with chamber 42 having a static capacity of about 250 microliters.

As indicated in FIGS. 2 and 3, the planar side wall surfaces 36, 38 of each chamber 40, 42 adjacent barrier 54 are connected by curved areas 62, 64, 66, 68 that provide smooth and gradual transitions between surfaces 58, 60 of barrier 54 and adjacent side wall surfaces 36, 38. These smoothly curved transition surfaces (of about 1.5 millimeter radius) are effective to retard spontaneous premixing capillary flow of reagent materials along those barrier-side wall intersections from one chamber to the other. Similar curved smooth and gradual surface intersection transitional areas 70, 72, 74, 76 extend away from barrier 54 in either direction along the intersections between side walls 36, 38 and adjacent base surfaces 44, 46. The gradual surface intersection transition areas 70, 72, 74, 76 taper at 78 to merge smoothly with capillary flow enhancing or "wicking" areas 80 in the form of abrupt surface intersections between the planar base and side walls of chambers 40 and 42, each abrupt intersection area 80 being adjacent the end of each chamber 40, 42 remote from barrier 54, and having a radius of about 0.5 millimeter. The intersection of planar vertical surface 60 of barrier 54 also has a smoothly curved gradual intersection 82 (of about 1.5 millimeter radius) with base 46 of chamber 42. Location of these reagent distribution surfaces may also be seen with reference to FIGS. 4, 5, and 6.

With reference to FIG. 7, a micropipetter—loader system station 88 has a reagent supply module 90, an indexed platform 92 that receives rotor 10 and a pipette arm 94 that carries two pipette tubes 96, 98. Module 90 includes a washbath 100, a first reagent supply 102 and a second reagent supply 104. A sample ring 106 which positions twenty sample cups 108 is placed concentrically around rotor 10. Samples, standards, and controls are placed in the sample cups 108 and reagents are poured into reagent supply containers 102, 104. Pipetter/loading control selections are made by setting mode switches on control panel 112. In response to depression of the start switch 114, pipetter arm 94 moves to washbath 100 where the tips are submerged and washed by raising the platform. The platform 92 then lowers and the pipette arm 94 travels to a position where the sample tube 96 is directly over a sample cup 108 and the reagent tube 98 is over reagent boat 104; the platform lifts and the pipette tips are dipped into the sample and reagent vessels, and preselected volumes of sample and reagent are picked up. The platform lowers and the pipette arm 94 moves to the corresponding sample and reagent ports 20, 18 in rotor 10. Again the rotor platform elevates and the aspirated sample and reagent volumes are dispensed into chambers 40, 42 of the aligned cuvette 30.

Where a second reagent is used, after washing the sample tip 96 is first positioned over and dipped into reagent container 102. After each cuvette loading cycle (of about thirty seconds in duration), rotor table 92 is indexed and the next cuvette is loaded in a similar cycle.

In this embodiment, a sample volume 2–20 microliters is dispensed into chamber 40 and a reagent volume of 150–200 microliters is dispensed into chamber 42 depending on the particular test involved. As the sample and reagent volumes flow into their respective cuvette chambers 40, 42, the transition areas 80 remote from barrier 54 wick or draw the liquids away from the barrier 54 towards the ends of the chambers while the gradual transition areas inhibit or retard the capillary flow of reagent material towards the crest 56 of barrier 54. This retarding action prevents spontaneous mixing of reagents between the two chamber compartments for thirty minutes or more, thus providing a cuvette loading interval without spontaneous premixing of at least one-half hour in this compact multi-cuvette type rotor.

After the rotor 10 has been completely loaded, it is transferred to an analyzer for incubation, centrifugal acceleration to provide transfer of the sample (and reagent) from chamber 40 to analysis chamber 42 and mixing. The rotor is then braked and then accelerated again to 1000 rpm for photometric analysis. The capillary flow inhibiting surfaces 62–67 retard spontaneous "creep" flow of reagent in either direction over the crest 56 of barrier 54 while not interferring with transfer of sample and reagent from chamber 40 to chamber 42 under centrifugal force nor with the mixing and analysis steps.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. An analysis cuvette for separately storing two reaction constituents, said analysis cuvette having a first condition in which said two constituents are stored separate from one another and a second condition in which said two reaction constituents are mixed together to form a reaction product for analysis comprising structure defining a first chamber region for receiving a first constituent and having a loading port through which said first constituent is introduced into said first chamber region, structure defining a second chamber region for storing a second constituent and defining a loading port through which said second constituent is introduced into said second chamber region, barrier structure between said first and second regions and structure defining a transfer passage between said first and second chamber regions, said barrier structure having a crest portion that defines the lower edge of said transfer passage, one of said constituents including sample material to be analyzed and the other constituent including reagent material for reaction with said one constituent material to provide a reaction product for analysis, said second chamber region including an analysis region where said reaction project is subjected to analysis, each said chamber region being defined by opposed planar side wall surfaces and a planar base wall surface, capillary flow inhibiting structure extending from the crest of said barrier structure along the intersections between said barrier structure and said side wall surfaces, and along a portion of the intersections between said side wall surfaces and said base surface of each chamber region.

2. The cuvette of claim 1 wherein said capillary flow inhibiting structure is a smoothly curved surface portion that has a radius greater than 0.75 millimeter.

3. The cuvette of claim 1 and further including capillary flow facilitating structure extending along each intersection between a chamber side wall surface and base wall surface at a location more remote from said barrier structure than said capillary flow inhibiting structure.

4. The cuvette of claim 3 wherein each said capillary flow facilitating structure is a wall intersection that has a radius of less than 0.75 millimeter.

5. The cuvette of claim 4 wherein said cuvette has a length of about four centimeters and a width of about one-half centimeter; and the crest of said barrier structure has a height of about one-quarter centimeter.

6. The cuvette of claim 5 wherein said analysis region is defined by first and second opposed optical windows.

7. The cuvette of any preceding claim wherein said barrier structure includes a ramp portion inclined at an angle of less than 30° that forms a wall of said first chamber region and a vertical wall surface that forms a wall of said second chamber region.

8. A multi-cuvette rotor for use in an analytical photometer that defines a circumferential array of elongated radially extending cuvettes, each said cuvette including the structure of any one of claims 1–6.

9. The rotor of claim 8 comprising a one-piece body member of molded transparent material with a planar upper surface and a circumferential array of elongated cuvette recesses with barrier structure in each said recess, and a one-piece cover member of molded transparent material that has a planar lower surface parallel to and immediately adjacent said planar upper surface of said body member with a continuous seal extending around each said cuvette recess between the upper and lower surfaces to define said circumferential array of analytical cuvettes.

* * * * *